(12) United States Patent
Balloni et al.

(10) Patent No.: US 6,348,793 B1
(45) Date of Patent: Feb. 19, 2002

(54) SYSTEM ARCHITECTURE FOR MEDICAL IMAGING SYSTEMS

(75) Inventors: William Balloni, Menomonee Falls; Josef Debbins, Waukesha; Robert Haworth, Brookfield; Paul Licato, Wauwatosa; Graeme C. McKinnon, Hartland; Bo J. Pettersson, Wauwatosa; Lawrence Ploetz, Brookfield; Mark Radick, Muskego, all of WI (US)

(73) Assignee: GE Medical Systems Global Technology, Company, LLC, Waukesha, WI (US)

(*) Notice: Subject to any disclaimer, the term of this patent is extended or adjusted under 35 U.S.C. 154(b) by 0 days.

(21) Appl. No.: 09/706,963

(22) Filed: Nov. 6, 2000

(51) Int. Cl.[7] .................................................. G01V 3/00
(52) U.S. Cl. ........................................ 324/309; 324/322
(58) Field of Search ................................. 324/309, 307, 324/308, 311, 312, 314, 318, 322; 600/410, 421; 705/2

(56) References Cited

U.S. PATENT DOCUMENTS

| | | | | |
|---|---|---|---|---|
| 6,157,194 A | * | 12/2000 | Vassallo et al. | 324/322 |
| 6,198,283 B1 | * | 3/2001 | Foo et al. | 324/309 |
| 6,272,469 B1 | * | 8/2001 | Koritzinsky et al. | 705/2 |

* cited by examiner

*Primary Examiner*—Louis Arana
(74) *Attorney, Agent, or Firm*—Quarles & Brady, LLP; Christian G. Cabou

(57) ABSTRACT

A medical imaging system includes a workstation for receiving operator inputs that prescribe a scan and a plurality of servers which control the acquisition of image data and the reconstruction of prescribed images. The workstation is programmed in Java™ to produce scan descriptions that are downloaded to the servers prior to run time using a serialization mechanism.

20 Claims, 4 Drawing Sheets

SYSTEM ARCHITECTURE FOR MEDICAL IMAGING SYSTEMS

BACKGROUND OF THE INVENTION

The field of the invention is medical imaging systems, and particularly, the hardware and software architecture of such systems.

There are many types of medical imaging systems. The primary distinction between the different systems is the medical imaging modality that is used, such as, x-ray, magnetic resonance, ultrasound or nuclear. In addition, a broad range of capabilities and features are typically offered in each imaging modality. For example, a magnetic resonance imaging ("MRI") system may be offered with a range of polarizing magnetic strengths and configurations and with a range of different optional features such as magnetic resonance angiography ("MRA"), cardiac imaging and functional magnetic resonance imaging ("fMRI").

Despite the many differences, medical imaging systems have a number of basic functions in common. All medical imaging systems include an operator interface which enables a particular image acquisition to be prescribed, a data acquisition apparatus which uses one of the imaging modalities to acquire data from the subject, an image reconstruction processor for reconstructing an image using acquired data, and storage apparatus for storing images and associated patient information. Typically, hardware is designed to carry out these functions and software is designed and written for each hardware configuration. When the hardware configuration is changed to take advantage of new concepts or new products, such as faster and more powerful microprocessors, much, if not all, of the software must be rewritten.

Another challenge to the designer of medical imaging equipment is the rapid improvements that are being made in the underlying science for each imaging modality. In magnetic resonance imaging, for example, new pulse sequences and related data acquisition methods are continuously being invented. To add such improvements to an existing MRI system typically requires the rewriting of system software as well as the addition of new, application specific software. The extent of this undertaking depends on the particular improvement being made and the nature of the particular system software architecture in place.

SUMMARY OF THE INVENTION

The present invention is a system architecture for a medical imaging system, and particularly, a new and improved software architecture for such systems. The architecture includes: a workstation that is programmed in a hardware independent language to provide an operator interface for receiving data which prescribes an image to be acquired, to produce an image acquisition description comprised of components which determine how the imaging system is to be operated to acquire image data, and to produce a data processing description comprised of components which determine how the acquired image data is processed to reconstruct an image; and a plurality of servers coupled to the workstation and being operable to receive the descriptions downloaded from the workstation and perform the indicated operations and processing. By employing a hardware independent language such as Java™, the workstation hardware may be changed with little or no changes to the software responsible for producing the descriptions. Similarly, much of the software employed by the servers to perform the downloaded descriptions may be machine independent.

Another aspect of the present invention is the manner in which the scan descriptions are downloaded to the servers. The workstation includes a serialization mechanism which sends the descriptions as a stream of components to their respective servers, and a deserialization mechanism at each server rebuilds the description so that it can direct the operation of the server during the scan.

GENERAL DESCRIPTION OF THE INVENTION

Figure 5:
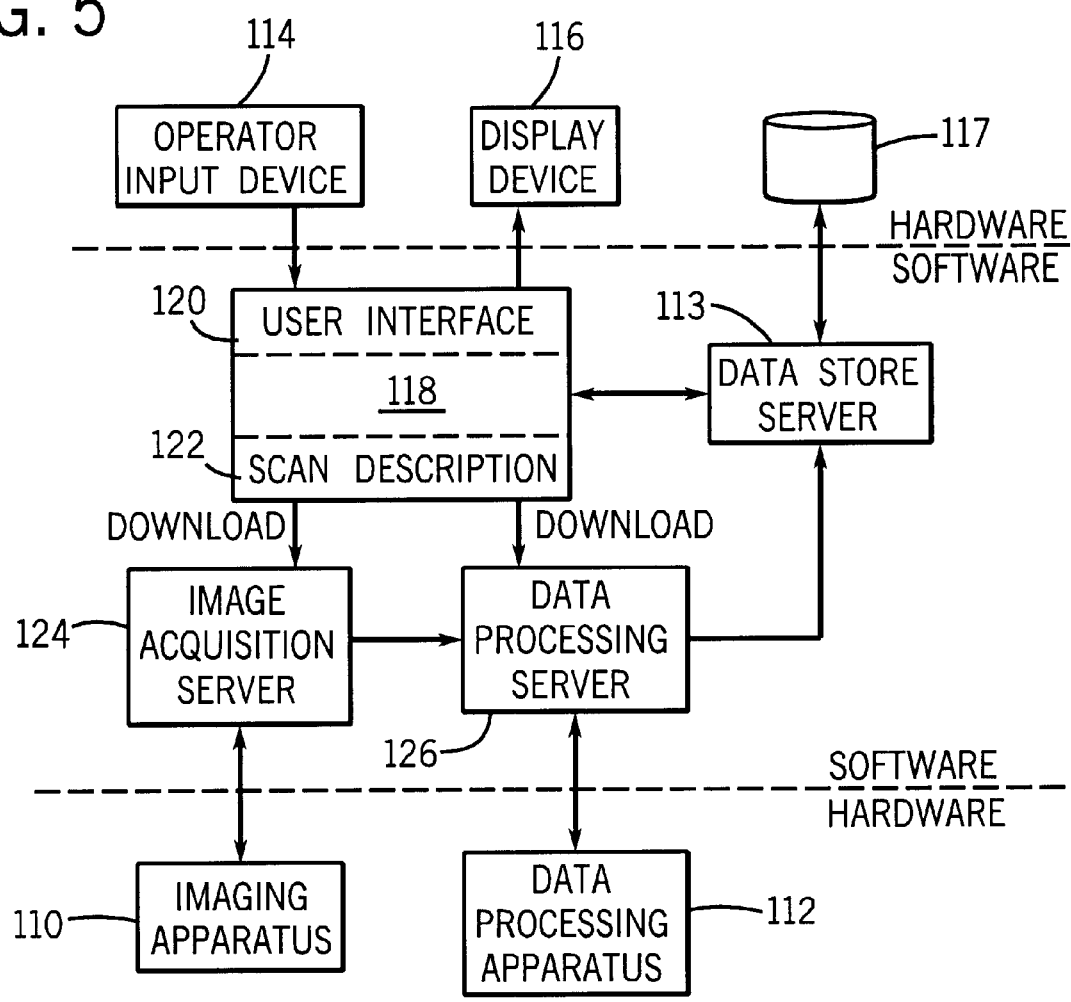
FIG. 5 is a block diagram of an imaging system which employs the present invention.

Referring particularly to FIG. 5, a medical imaging system includes imaging apparatus 110 comprised of mechanical and electrical hardware elements that are operated during a scan to acquire image data. The imaging system also includes data processing apparatus 112 that is operated to reconstruct images using the acquired image data. To operate the system and to enter a scan prescription an operator input device 114, such as a keyboard and control panel, is provided, a display device 116 is provided to present the images for visualization and a storage device 117, such as a hard disc drive, is provided to archive acquired images. The particular imaging modality used, and the complexity and power of these hardware elements varies substantially from one system to the next.

The present invention includes a workstation 118 which is programmed in a machine independent language, such as Java™, to provide a user interface 120 that enables an operator to enter scan parameters using the operator input device 114. The workstation 118 is programmed to produce a scan description 122, which in its simplest configuration contains image acquisition description components and data processing description components that contain information required by the imaging apparatus 110 and data processing apparatus 112 to perform the prescribed scan.

Prior to run time, a snap shot of the scan description 122 is downloaded to a plurality of servers which control the imaging system hardware apparatus. In the simplest configuration these include an image acquisition server 124 and a data processing server 126 which operate the respective imaging apparatus 110 and data processing apparatus 112. When provided with the scan description components, the servers' programs direct the image system hardware apparatus to perform the prescribed scan. A data store server 113 directs the storage device 117 to save the images along with associated patient information.

The software elements can be easily configured to run on different hardware. The workstation 118 and servers 113, 124 and 126 can run on separate programmable machines, or one or more may run on the same programmable machine. The data processing server 126 or data store server 113 may run on the data processing apparatus 112 or on the workstation 118. Regardless of the configuration, because the workstation 118 is programmed in a machine independent language, it is easily transported to run on different programmable machines. In addition, even though the servers 113, 124 and 126 may be changed to run on different programmable machines, little change is required in the workstation 118 because the scan description can remain unchanged. With changes in servers, the only changes required in the workstation 118 may be minor differences in the particular scan description components that are downloaded to the servers.

The number of servers may also be increased without the need for substantial changes in the workstation 118. For example, if the image acquisition server 124 is split into two or more separate servers, the only substantial change in the workstation 118 is to download the appropriate description components to each server.

To accommodate the variety of hardware systems that may be used, applications are written in a hardware independent format such as the Java™ class file format. Object-oriented applications are formed from multiple class files that are accessed from servers and downloaded individually as needed. Class files contain byte code instructions. A "virtual machine" process that executes on a specific hardware platform loads the individual class files and executes the byte codes contained within.

The present invention is preferably implemented using object-oriented programming methods. Object-oriented programming is a method of creating computer programs by combining certain fundamental building blocks, and creating relationships among and between the building blocks. The building blocks in object-oriented programming systems are called "objects". An object is a programming unit that groups together a data structure (one or more instance variables) and the operations (methods) that can use or affect that data. Thus, an object consists of data and one or more operations or procedures that can be performed on that data. The joining of data and operations into a unitary building block is called "encapsulation".

An object can be instructed to perform one of its methods when it receives a "message". A message is a command or instruction sent to the object to execute a certain method. A message consists of a method selection (e.g., method name) and a plurality of arguments. A message tells the receiving object what operations to perform.

One advantage of object-oriented programming is the way in which methods are invoked. When a message is sent to an object, it is not necessary for the message to instruct the object how to perform a certain method. It is only necessary to request that the object execute the method.

Object-oriented programming languages are predominantly based on a "class" scheme. A class defines a type of object that typically includes both variables and methods for the class. An object class is used to create a particular instance of an object. An instance of an object class includes the variables and methods defined for the class. Multiple instances of the same class can be created from an object class. Each instance that is created from the object class is said to be of the same type or class.

An object is a generic term that is used in the object-oriented programming environment to refer to a module that contains related code and variables. A software application is written using an object-oriented programming language whereby the program's functionality is implemented using objects.

A Java™ program is composed of a number of classes and interfaces. Unlike many programming languages, in which a program is compiled into machine-dependent, executable program code, Java™ classes are compiled into machine independent bytecode class files. Each class contains code and data in a platform-independent format called the class file format. The computer system acting as the execution vehicle contains a program called a virtual machine, which is responsible for executing the code in Java™ classes. The virtual machine provides a level of abstraction between the machine independence of the bytecode classes and the machine-dependent instruction set of the underlying computer hardware. A "class loader" within the virtual machine is responsible for loading the bytecode class files as needed, and either an interpreter executes the bytecodes directly, or a "just-in-time" compiler transforms the bytecodes into machine code, so that they can be executed by the processor.

DESCRIPTION OF THE PREFERRED EMBODIMENT

Figure 1:
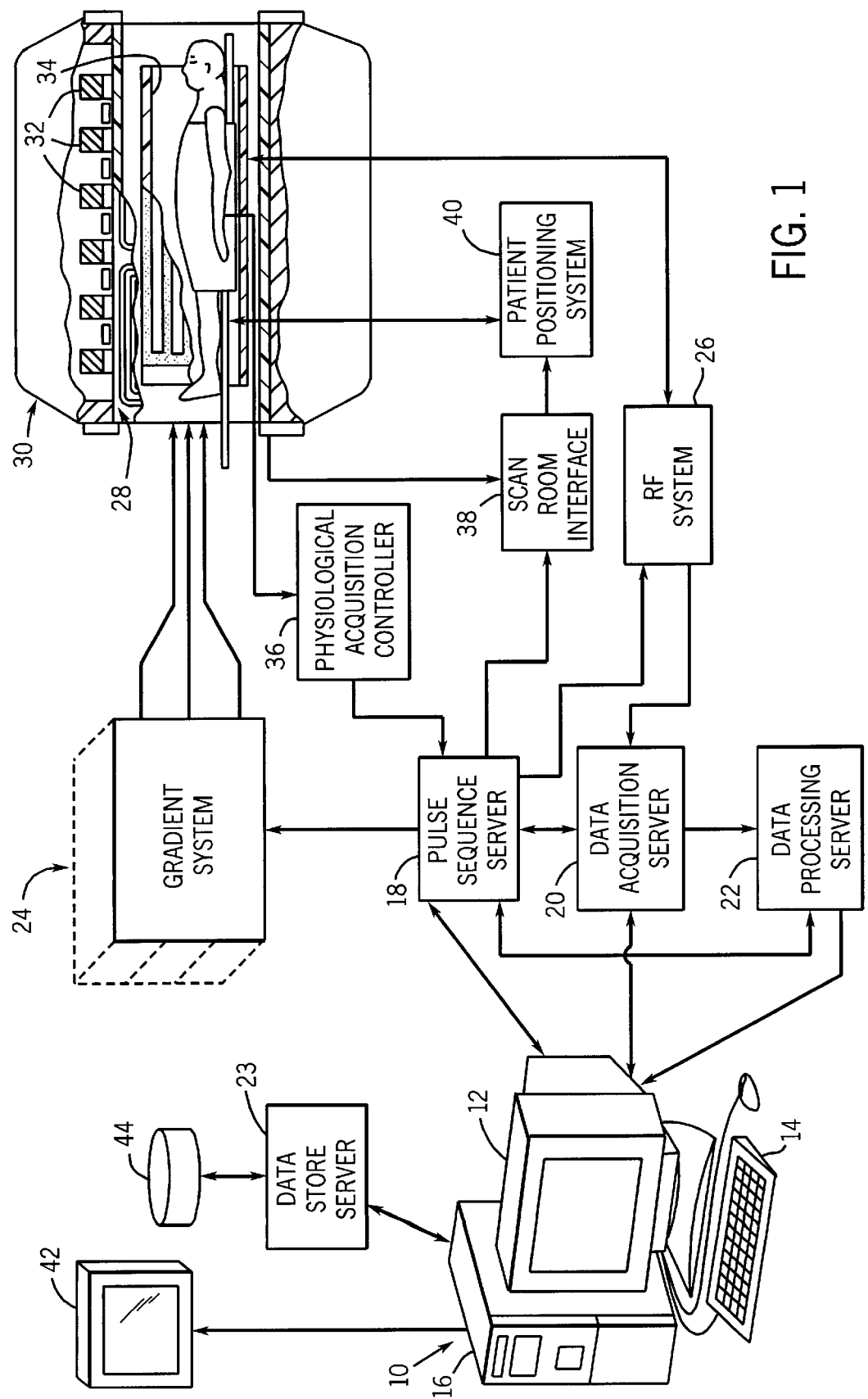
FIG. 1 is a block diagram of an MRI system which employs the preferred embodiment of the invention.

Referring particularly to FIG. 1, the preferred embodiment of the invention is employed in an MRI system. The MRI system includes a workstation 10 having a display 12 and a keyboard 14. The workstation 10 includes a processor 16 which is a programmable machine commercially available from Silicon Graphics, Inc. It is based on a 64-bit microprocessor manufactured by Intel and it runs the Linux operating system. The workstation 10 provides the operator interface which enables scan prescriptions to be entered into the MRI system. As will be described in more detail below, the workstation 10 will run one or more Java™ virtual machines which will run code which is programmed in the Java™ language that is fully transportable to any other programmable machine which is Java™ compatible. The programs which implement the operator interface are thus written in a language which is hardware independent. This means that the same Java™ programs can be run on workstations having different hardware configurations and capabilities and they can easily migrate to newer programmable machines that are developed to take advantage of the rapid advances in integrated circuit technology.

The workstation 10 is coupled to four servers: a pulse sequence server 18; a data acquisition server 20; a data processing server 22, and a data store server 23. In the preferred embodiment the data store server 23 is performed by the workstation processor 16 and associated disc drive interface circuitry. The remaining three servers 18, 20 and 22 are performed by separate processors mounted in a single enclosure and interconnected using a 64-bit backplane bus structure based on the PCI standard for industrial and telecommunications applications called "CompactPCI". The pulse sequence server 18 employs a 366 MHz microprocessor model PPC750 and a quad communication controller model MPC860T manufactured by Motorola, Inc. The data acquisition server 20 and data processing server 22 both employ the same 366 MHz microprocessor and the data processing server 22 further includes one or more array processors based on parallel vector processors commercially available from Mercury Computer Systems, Inc. as the PowerPC™. Another 366 MHz microprocessor (not shown) serves as a hardware controller on the PCI bus structure and it controls a quad communication controller model MPC860T manufactured by Motorola, Inc.

The workstation 10 and each processor for the servers 18, 20 and 22 are connected to a 100 BaseT Ethernet serial communications network. As will be explained in more detail below, this serial network conveys data that is downloaded to the servers 18, 20 and 22 from the workstation 10 and it conveys tag data that is communicated between the servers and between the workstation and the servers. In addition, a high speed data link using the BIT3 protocol is provided between the data processing server 22 and the workstation 10 in order to convey image data to the data store server 23.

The pulse sequence server 18 functions in response to program elements downloaded from the workstation 10 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$ and $G_z$ used for position encoding NMR signals. The gradient coil assembly 28 forms part of a magnet assembly 30 which includes a polarizing magnet 32 and a whole-body RF coil 34.

RF excitation waveforms are applied to the RF coil 34 by the RF system 26 to perform the prescribed magnetic resonance sequence. Responsive NMR signals detected by the RF coil 34 are received by the RF system 26, amplified, demodulated, filtered and digitized under direction of commands produced by the pulse sequence server 18. Exemplary RF systems are described in U.S. Pat. No. 4,952,877 and U.S. Pat. No. 4,992,736.

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize the performance of the scan.

The pulse sequence server 18 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

It should be apparent that the pulse sequence server 18 performs real-time control of MRI system elements during a scan. As a result, it is necessary that its hardware elements be operated with program instructions that are executed in a timely manner. As will be explained in more detail below, the pulse sequence server 18 is controlled during run-time by programs written in a low level programming language such as assembler, C or C++. The description components for a scan prescription are downloaded from the workstation 10 in the form of objects. The pulse sequence server 18 contains programs which receive these objects using a deserialization mechanism. The pulse sequence server 18 also includes a program which converts the objects to C++ objects that are employed by the run-time programs. In the preferred embodiment Java™ objects are downloaded and the Java™ serialization mechanism is employed. The pulse sequence server 18 thus includes both hardware independent programs written in Java™ and hardware dependent programs. It is contemplated that Java™ interpreters will eventually become fast enough that nearly all programs run on the pulse sequence server 18 will be written in hardware independent form.

The digitized NMR signal samples produced by the RF system 26 are received by the data acquisition server 20. The data acquisition server 20 operates in response to description components downloaded from the workstation 10 to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan as described in co-pending U.S. patent application Ser. No. 08/635,078 filed Apr. 19, 1996 and entitled "Method For Performing Magnetic Resonance Angiography Using a Contrast Agent". In all these examples the data acquisition server 20 acquires NMR data and processes it in real-time to produce information which is used to control the scan.

As with the pulse sequence server 18, the hardware elements of the data acquisition server 20 are operated at run-time with program instructions in a programming language such as assembler, C or C++. As will be explained in more detail below, the directions for its operation during a scan are downloaded from the workstation 10 in the form of objects. A server proxy receives the objects using the serialization mechanism and the downloaded objects are converted to C++ objects that are employed to operate the data acquisition server 20 during run-time. As indicated above, Java™ objects are downloaded in the preferred embodiment using the Java™ serialization mechanism.

The data processing server 22 receives NMR data from the data acquisition server 20 and processes it in accordance with description components downloaded from the workstation 10. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display 42 which is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Directions for the particular operations to be performed by the data processing server 22 are downloaded from the workstation 10 as will be described in more detail below. The time critical functions are performed with programs written in assembler, C or C++ and the downloaded Java™ object directions must be converted to corresponding executable code as described above.

Figure 2:
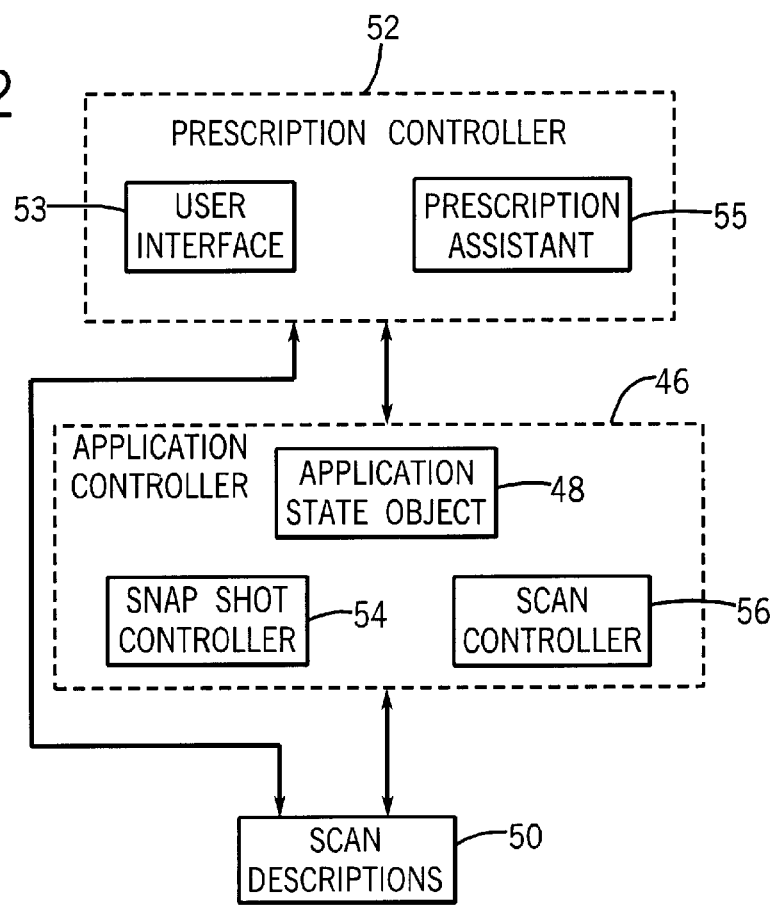
FIG. 2 is a block diagram of functional components in a workstation which forms part of the MRI system of FIG. 1.

As indicated above, the workstation 10 contains a Java™ virtual machine which executes programs written in the Java™ programming language. The workstation software is structured to perform "applications" which may be selected and run by an operator. Such applications correspond to clinical imaging procedures and may include, for example:

perform a scan using an FSE pulse sequence;
conduct a CEMRA dynamic study;
perform an fMRI study;
perform a runoff vascular study
perform image post processing
filming
networking An application is a collection of Java™ objects stored in an "application container" that may be selected by an operator to perform a scan. Referring particularly to FIG. 2, each application container includes a Java™ application controller component 46 which directs other Java™ components in the container to perform the scan. These other components include a prescription controller 52 which includes a user interface component 53 and a prescription assistant component 55 that enable an operator to control the procedure performed by the application.

The application container also includes scan descriptions 50. As will be described in more detail below, these scan descriptions are downloaded to the servers 18, 20, 22 and 23 (FIG. 1) and used by those servers to perform the prescribed scan. The stored scan descriptions 50 are unique for every different application, however, further information may be entered by the operator to fully prescribe the scan.

The application controller 46 includes an application state object 48 which maintains the state of the application as the scan is performed. The possible states during a life cycle of an application are as follows:

Initialization
Prescribing
Prescribed
Downloading
Downloaded
Prescanning
Prescanned
Batch Scanning
Real Time Scanning
Scan Paused
Scanned
Reconstructed
Visualized. This life cycle is driven by commands from the application container (like initialize application), by commands from the operator (like start scan) and by commands generated internally by the application (like scan done).

When the operator selects an application, the application initializes and changes to the "prescribing state" and the prescription controller 52 is enabled to interact with the scan description components 50 to determine what scan parameters must be specified by the operator (e.g. TR, number of slices, location of FOV, flip angle) and determine if the prescription is complete and valid. The prescription controller 52 then signals the application state object 48 to switch to the "prescribed" state and download, prescan and scan buttons on the control panel are enabled.

If the operator hits the "download" button, the application state object 48 changes to the "download state" and the application controller 46 employs a snap shot controller 54 to issue snap shot and download commands. As will be described in more detail below, these commands cause the scan descriptions 50 to be downloaded to the servers 18, 20, 22 and 23. The snap shot controller 54 receives "download done" notification back from each of the servers 18, 20 and 22, and when all four servers have been downloaded, the application state object 48 is changed to the "downloaded" state.

If the operator hits the scan button, the application state object 48 will change to the scan mode and a scan controller 56 is employed to issue a scan command to the pulse sequence server 18. The next state transition is governed by the scanning mode i.e., real-time or batch. The behavior of the application in the two modes is very different and so there are two different scanning states. If in real-time mode, the application is set to a "real-time scanning" state and if in batch mode, the application state is set to a "batch scanning" state. When in the real-time mode, if the user chooses to pause the scan, the application will transition to a "scan paused" state. If scanning is resumed, the application goes back to the real-time scanning state. In real-time scanning state, the application can be edited and edited descriptions will be downloaded even while the scanning is in progress. However, the application will not make a state transition; instead, the same state will be characterized to allow editing and downloading. It is this behavior of the real-time scanning state that differentiates it from the batch scanning state.

The application will make a transition to the "scanned" state when the operator hits the "stop scan" button. Also, if the application is in the batch scanning mode of operation, the pulse sequence server 18 notifies the application controller 46 when the scan is completed. The application state object changes to the "scanned" state in either event.

When the data processing server 22 completes reconstruction of the acquired images, the application controller 46 is notified and the application state object 48 is changed to the "reconstructed" state. This indicates to the workstation 10 that reconstructed images are available on disk 44 for display or further processing.

Figure 3:
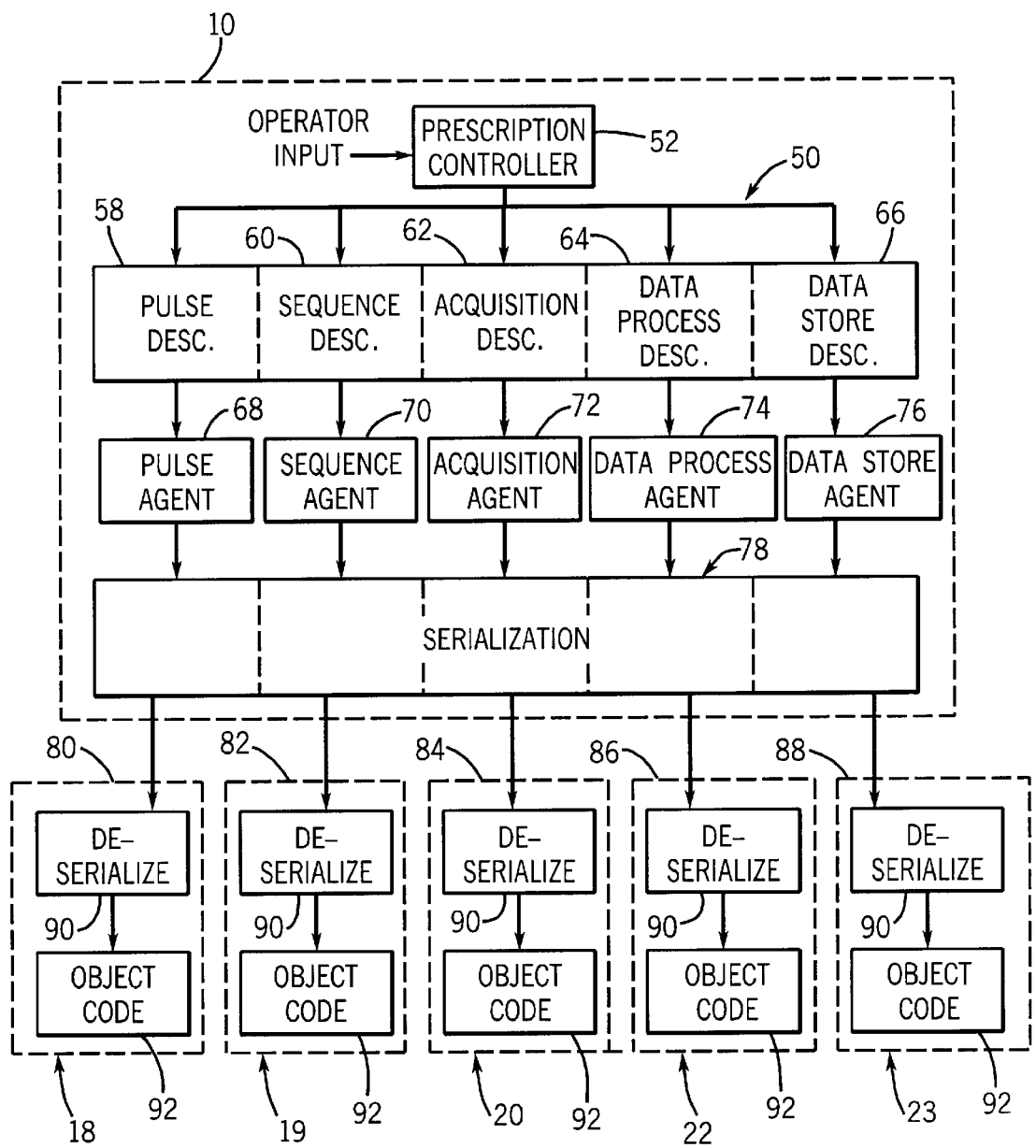
FIG. 3 is a block diagram of functional and data components in the MRI system of FIG. 1 which illustrate a download event.

Referring particularly to FIG. 3, the scan descriptions 50 contain a set of components that serve to collect scan parameters using the prescription controller 52, and to organize those prescription scan parameters into a set of smaller components that can be downloaded to the servers 18, 20, 22 and 23. On the servers 18, 20 and 22, those downloaded components direct the operation of the hardware in order to carry out the prescribed scan.

There are different description types within each application to provide logical groupings of components to deal with different aspects of executing an MR scan. These description types are:

Pulse Description 58;
Sequence Description 60;
Acquisition Description 62;
Data Processing Description 64;
Data Store Description 66. The pulse description 58 includes components that define and control the waveforms to be played out on the gradient system and the RF system hardware, along with hardware control components. These components control the dynamic aspects of the waveforms and hardware in response to events produced at run-time by components of the sequence description. This description 58 also includes components that control the filtering of NMR signals received by the RF system 26. These components collectively define a unique set of gradient/RF/control pulses which are used to excite, encode, and readout the NMR signals. Examples are pulse descriptions for 2D spin echo, 2D gradient-echo, 2D fast spin-echo, and 3D gradient-echo sequences.

The sequence description 60 includes a set of components that control the order of pulse sequences played out, and define a series of prescribed events along the scan timeline. These prescribed events defined by the sequence description 60 trigger the dynamic behavior of the pulse components in pulse description 58. These components prescribe a unique acquisition ordering used to define the slice and k-space sampling order. Examples are 2D sequential, 2D interleaved, 3D sequential, 3D elliptical centric, and multi-slice CINE.

The acquisition description 62 includes a set of components that prescribe the real-time processing of NMR signals acquired by the RF system 26. These components direct the performance of operations on acquired NMR signals to produce information that is fed back to components in the sequence description 60 to affect subsequent scanner operation. These components may, for example, process NMR signals during a prescan to feedback changes in the power or frequency of RF pulses produced during the subsequent scan; or process NMR signals to detect when a bolus of contrast agent arrives in a region of interest and trigger the start of a centric view order acquisition; or process "navigator" NMR signals to produce phase correction information which may be used to alter the view order of the scan or alter the demodulation reference frequency of the RF system 26. There are scans commonly used in clinical applications which do not require this capability, however, and in those applications, the components in the acquisition description 62 simply buffer the acquired NMR signals and make them available to the data processing server 22.

The data processing description 64 contains components that direct the data processing server 22 to transform acquired NMR signals into a meaningful form. Image reconstruction is the most common function and the resulting form is a 2D or 3D image of the subject being scanned. Spectroscopy processing can also be defined by these components, in which case the form that results is an image of the spectra of the acquired NMR signals.

The data store description 66 contains components that define the images which are stored in the database during a scan. In addition to the reconstructed images, this may include patient information and scan parameter information which is to appear on the image along with the patient anatomic or spectrographic information.

Referring particularly to FIGS. 2 and 3, after the prescription is completely entered and the scan descriptions 50 are completed, a download may be initiated and the snap shot controller 54 operates to transfer components in the scan descriptions 50 to the servers 18, 20 and 22. This is accomplished by forming agents 68, 70, 72, 74 and 76 from components in the respective descriptions 58, 60, 62, 64 and 66. Each resulting agent includes a set of objects that can direct the operation of a server to carry out tasks during the scan. To transfer downloadable components to a server, an agent uses serialization indicated at process block 78. Serialization transforms the agent's objects into a stream format that maintains the name of the object class, the instances of their data, and the references between objects. When first initialized, the agent registers with the snap shot controller 54. When the prescription is complete, the snap shot controller 54 informs the agent that it is to take a snap shot. The agent serializes itself and all of its downloadable components, then hands that data stream and the identity of the target server to a snap shot object. That snap shot object is passed to the target server to complete the download.

The serialization mechanism is a standard feature in Java™ which allows objects to be written to an output data stream as described, for example, in U.S. Pat. No. 6,092,120, issued on Jul. 18, 2000 and entitled "Method And Apparatus For Timely Delivery Of A Byte Code And Serialized Object" which is incorporated herein by reference. The data stream can be passed across process boundaries, or saved to disk to retain the state of the objects for later use. The serialized object data stream carries the class name of each object and that object's instance data described by attribute name, type, and value. A powerful aspect of serialization is the ability to capture the relationships between objects when the data stream is received and deserialized. This allows a graph of objects to be captured in the serialized stream and then recreated at a later time or on a different machine. The serialization mechanism captures all relationships between objects. Each object in the graph is only serialized once. Should one object be referenced more than one time, the serialization mechanism recognizes the repeat and inserts a reference to the previous occurrence in the stream. This prevents endless loops during serialization and the potential for stream bloat due to duplication of objects. It is important to note that the serialized data stream only contains the object data and does not include object method code, the executable portion of the object. This substantially reduces the amount of data downloaded to the servers by the snap shot controller 54. It also requires that object method code be resident on each server.

Referring particularly to FIG. 3, the serialized agents 68, 70, 72, 74 and 76 are downloaded to corresponding functional servers 80, 82, 84, 86 and 88. Functional servers 80, 82, 84 and 86 reside on the three servers 18, 20 and 22 and the data is conveyed through an Ethernet serial communications network. The pulse server 80 and the sequence server 82 reside on the pulse sequence server hardware 18, the acquisition server 84 resides on the data acquisition server hardware 20, and the data process server 86 resides on server hardware 20 or 22. The data store server 88 resides on the workstation 10. It should be apparent to those skilled in the art that the functional servers may reside on many different hardware combinations and that the present architecture facilitates the use of different hardware combinations. If different server hardware is used, the only change required in the workstation software is the agent which groups description components specifically targeted for the new server hardware. The new agent is constructed using components in the existing scan descriptions 50 and it is created and downloaded using existing software as described above.

The serialized agents are received by the corresponding target functional servers when a snap shot download event is generated by the snap shot controller 54. Each stream of serialized agents must be deserialized as indicated at process blocks 90. If the servers are written in Java™, this deserialization is a standard feature of the language as described, for example in the above cited U.S. Pat. No. 6,092,120. As indicated above, however, in the preferred embodiment the servers employ C++ object code and the deserialization requires some extra effort. To perform the deserialization the servers use a commercially available software product available from Rogue Wave Software, Inc. of Boulder Colorado. This product provides a C++ library for restoration of the Java™ object stream. This tool is able to parse the Java™ stream and present the contained class names, attributes, and object relationships to reader writer classes. Each C++ component that is to be created from the stream must have a reader writer. This class maps the parsed information to appropriate constructors and set methods of the C++ objects.

As stated previously, the serialized stream does not contain code, only instance data for the objects. The code for the C++ classes resides on the server. Every type of Java™ agent and Java™ downloadable component has a mirror C++ object on the server. The mirrored components must have the same class name and share a common set of attributes. At the completion of the deserialization process, executable object code indicated at 92 resides in each of the functional servers 80, 82, 84, 86 and 88. Each functional server does the equivalent of signaling the snap shot controller 54 in the workstation 10 when the download is completed and the application state object 48 changes to the "downloaded" state.

When the operator hits the "run" button on the control panel, the scan controller 56 coordinates the run time operation of the workstation and the servers to perform the scan. To do this, the scan controller 56 may communicate with the functional servers 80, 82, 84, 86 and 88 across a number of different bus structures, backplanes and serial communications networks. For example, the scan controller 56 signals the pulse sequence server 18 to start the scan, and it receives a notice from the data processing server 22 when images are available to view. In addition, the functional servers must communicate with each other during the scan. For example, the pulse server 80 and the sequence server 82 operate in close coordination using the corresponding downloaded agents to produce the desired pulses in the required sequence and with the required timing. The acquisition server 84 may send information back to servers 80 or 82 to alter a pulse or the sequence during the scan. Image data acquired by the acquisition server 84 is passed on to the data process server 86 and the data store server 88 receives information from both the data process server 86 and the workstation 10 to carry out its function of merging patient information with reconstructed images.

This run-time communications is provided by a tagged data transfer system. Tagged data transfer is a system that isolates applications/servers from hardware dependencies by providing tag (data packet) representation and routing mechanisms with different low level communication schemes. A tagged data packet consists of a header and a payload. The header contains information useful for interpreting the payload such as Id, Tagged Data Type, Payload Size, Byte Order, Hop Count, etc. The Payload contains the platform independent data or tagged data object. The data being passed can be transferred and interpreted in-process or inter-process including processes distributed across different programmable machines.

| Tagged Data: |
|---|
| Header |
| Id |
| Type |
| PayloadSize |
| ByteOrder |
| PayLoad |

Figure 4:
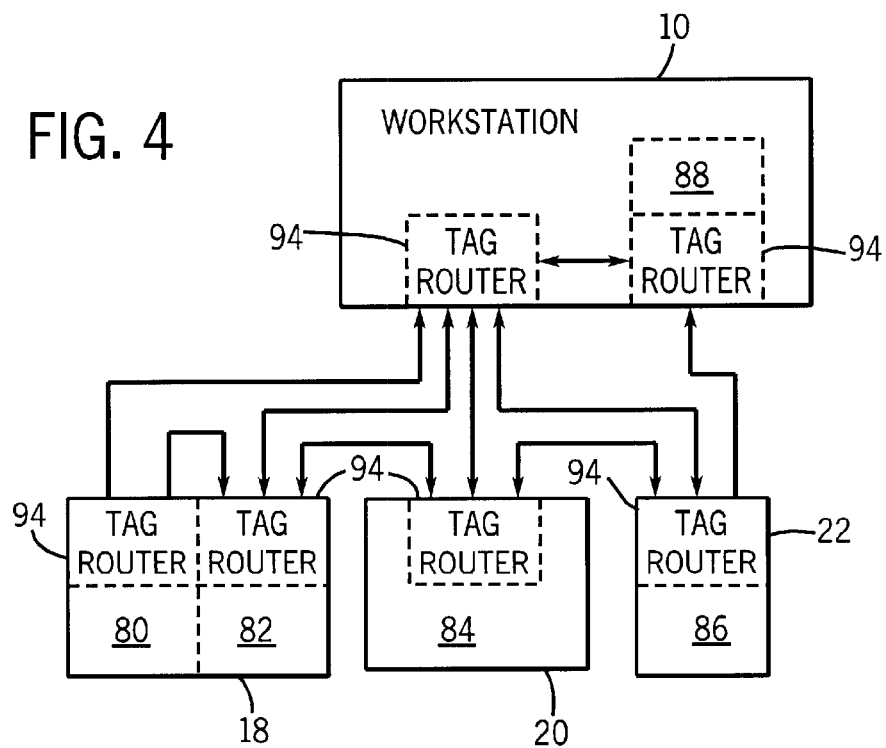
FIG. 4 is a block diagram of elements in the MRI system of FIG. 1 which illustrate the tag communication system.

Tagged data objects are created by requesting a tagged data system singleton. The data to be transported is passed to the tagged data system in the form of a taggable. Data can be appended, removed, and updated in a tagged data object. Then the tagged data object is sent to a tag router, which takes care of sending the data to its destination. As shown in FIG. 4, the workstation 10 and each of the functional servers 80, 82, 84, 86 and 88 includes a tag router 94. These are written in Java™ and in C++ and they communicate with each other using the available communications hardware and protocols. Any process interested in receiving tagged data has a logical address which it registers with the local tag router. Such registration includes providing its reference. The reference contains information about the process/server id, application id, snap shot and the agent/component id. Each process thus has at least one tag router which enables tagged data transfer with other processes.

A tag router maintains data transfer channels which resemble stream pipes. These channels hide the low level communication details from the tag router and provide a mechanism to transport tagged data to its peer in another process space. A channel consists of an incoming data channel and an outgoing data channel. The in and out channels indicate a queuing/dequeuing scheme and communications schemes. A sending process has the option of getting notification upon the failure or success of the tag send operation. The sending process can also specify the queue size on incoming and outgoing channels.

The DICOM standard is used to represent data and hence achieve platform independence. The Digital Imaging and Communications in Medicine standard was developed by the American College of Radiology and the National Electrical Manufacturers Association to provide a standard for transferring medical images and associated information between devices. The data types in DICOM are well defined, and are hardware independent. Predefined DICOM tags can be used to identify data that is being transmitted and packets can be easily extended by application programmers. The data types supported are a subset of those specified by the DICOM specification, including string, integer, and floating point.

The Java™-based infrastructure provided by the system architecture of the present invention facilitates changes in system hardware, changes in clinical applications, and the addition of new clinical procedures. The workstation is highly transportable from one program machine to another as long as both are configured to have Java™ virtual machines. The servers contain hardware dependent programs which require changes when changes are made in the system hardware they control. But such changes are primarily limited to the servers. It may be necessary to change the agent in the workstation which corresponds to a changed server, but this is a well defined task that does not impact other aspects of the workstation operation.

The addition of new clinical applications to the MRI system requires the addition of a new application container. The Java™-based infrastructure provides objects which perform the downloading and tag communications functions. The details of how these functions are performed over the particular system serial links and backplanes is transparent to the application programmer who can focus on defining the correct pulses, pulse sequence, and NMR data acquisition and processing functions for the clinical application.

What is claimed is:

1. A medical imaging system, the combination comprising:
   a) a workstation programmed in a hardware independent programming language to provide:
      i) an operator interface for receiving input information which prescribes a scan to be performed;
      ii) an image acquisition description comprised of components which determine how the imaging system is to operate during the scan to acquire image data; and
      iii) a data processing description comprised of components which determine how the acquired image data is processed to reconstruct an image; and
   b) a plurality of servers coupled to the workstation and being operable to receive the descriptions downloaded from the workstation, each server being operable in response to downloaded descriptions to perform functions during the scan.

2. The medical imaging system as recited in claim 1 in which the hardware independent programming language is an object oriented language.

3. The medical imaging system as recited in claim 1 in which the hardware independent programming language is Java™.

4. The medical imaging system as recited in claim 2 in which components of the descriptions are downloaded as streams of objects.

5. The medical imaging system as recited in claim 1 in which the work station is further programmed to provide:

a plurality of agents, each agent corresponding to one of the plurality of servers and each agent including components selected from a description; and means for downloading each agent to its corresponding server.

6. The medical imaging system as recited in claim 5 in which the means for downloading each agent includes a serialization mechanism at the workstation and a deserialization mechanism at each server.

7. The medical imaging system as recited in claim 1 in which the workstation resides on one programmable machine and at least one of the servers resides on a second programmable machine.

8. A magnetic resonance imaging (MRI) system which comprises:

a) a workstation programmed to provide:
      i) an operator interface for receiving input information which prescribes a scan to be performed;
      ii) a pulse description comprised of components which determine the pulses produced during the scan;
      iii) a sequence description comprised of components which determine the pulse sequence used during the scan to acquire NMR signals;
      iv) a data process description comprised of components which determine how the acquired NMR signals are processed into a clinically useful form; and
   b) a plurality of servers coupled to the workstation and being operable to receive the descriptions downloaded from the workstation, each server being operable in response to downloaded descriptions to operate elements of the MRI system to perform the scan.

9. The MRI system as recited in claim 8 in which one of the servers controls a gradient system and an RF system on the MRI system.

10. The MRI system as recited in claim 9 in which another one of the servers reconstructs images from NMR signals produced by the RF system.

11. The MRI system as recited in claim 10 in which the workstation resides on one programmable machine, the one server resides on a second programmable machine, and the other one of the servers resides on a third programmable machine.

12. The MRI system as recited in claim 8 in which the workstation further includes:

v) an acquisition description comprised of components which direct the acquisition of NMR signals and the production of information therefrom that is used to control the scan.

13. The MRI system as recited in claim 12 in which the workstation further includes:

iv) a data store description comprised of components which direct the merger of images produced under the direction of the data process description with information pertaining to the subject of the image.

14. The MRI system as recited in claim 13 in which there is a corresponding server for each description and in which components in each of the descriptions is downloaded to its corresponding server to enable the MRI system to perform the prescribed scan.

15. The MRI system as recited in claim 14 in which the workstation is further programmed to provide:

a plurality of agents, each agent corresponding to one of the plurality of servers and each agent including components selected from a description; and means for downloading each agent to its corresponding server prior to performing the scan.

16. The MRI system as recited in claim 15 in which the means for downloading each agent includes a serialization mechanism at the workstation and a deserialization mechanism at each server.

17. The MRI system as recited in claim 16 in which the programs employed by the workstation are written in a machine independent language.

18. The MRI system as recited in claim 17 which the workstation includes a Java™ virtual machine and the programs are written in Java™.

19. The MRI system as recited in claim 8 in which the workstation is further programmed to provide:

a plurality of agents, each agent corresponding to one of the plurality of servers and each agent including components selected from a description; and means for downloading each agent to its corresponding server.

20. The MRI system as recited in claim 19 in which the means for downloading each agent includes a serialization mechanism at the workstation and a deserialization mechanism at each server.

* * * * *